(12) United States Patent
Vass et al.

(10) Patent No.: US 7,778,686 B2
(45) Date of Patent: *Aug. 17, 2010

(54) METHOD AND APPARATUS FOR MEDICAL INTERVENTION PROCEDURE PLANNING AND LOCATION AND NAVIGATION OF AN INTERVENTION TOOL

(75) Inventors: Melissa Vass, Milwaukee, WI (US); Jasbir S. Sra, W. 305 N.29263 Red Oak Ct., Pewaukee, WI (US) 53072

(73) Assignees: General Electric Company, Schenectady, NY (US); Jasbir S. Sra, Pewaukee, WI (US)

(*) Notice: Subject to any disclaimer, the term of this patent is extended or adjusted under 35 U.S.C. 154(b) by 817 days.

This patent is subject to a terminal disclaimer.

(21) Appl. No.: 10/710,923

(22) Filed: Aug. 12, 2004

(65) Prior Publication Data

US 2005/0080328 A1 Apr. 14, 2005

Related U.S. Application Data

(63) Continuation-in-part of application No. 10/065,595, filed on Nov. 1, 2002, now Pat. No. 7,346,381.

(60) Provisional application No. 60/385,749, filed on Jun. 4, 2002, provisional application No. 60/494,607, filed on Aug. 12, 2003.

(51) Int. Cl.
*A61B 5/00* (2006.01)

(52) U.S. Cl. ..................................... 600/424

(58) Field of Classification Search ................. 600/407, 600/424, 425–427; 128/920, 922; 382/128, 382/130, 131
See application file for complete search history.

(56) References Cited

U.S. PATENT DOCUMENTS

| | | | |
|---|---|---|---|
| 3,954,098 A | 5/1976 | Dick et al. | 128/2.05 Z |
| 4,364,397 A | 12/1982 | Citron et al. | |
| 4,574,807 A | 3/1986 | Hewson et al. | 128/419 PG |
| 5,245,287 A | 9/1993 | Nowak et al. | 324/322 |
| 5,274,551 A | 12/1993 | Corby, Jr. | 364/413.13 |
| 5,304,212 A | 4/1994 | Czeisler et al. | 607/88 |
| 5,348,020 A | 9/1994 | Hutson | 128/696 |

(Continued)

FOREIGN PATENT DOCUMENTS

| EP | 1182619 A2 | 2/2002 |
|---|---|---|
| EP | 1321101 A2 | 12/2002 |
| WO | WO 91/07726 | 5/1991 |
| WO | WO 96/10949 | 4/1996 |

OTHER PUBLICATIONS

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" Circulation 1996; 94:407-24.

(Continued)

*Primary Examiner*—Brian Casler
*Assistant Examiner*—Jonathan G Cwern
(74) *Attorney, Agent, or Firm*—Cantor Colburn LLP

(57) ABSTRACT

A system and method for a medical intervention procedure within a cardiac chamber having an imaging system to obtain image data of the cardiac chamber and to create a 3D model from that image data, an interventional system to register the 3D model with a real-time image of the cardiac chamber and to display the 3D model, and an interventional tool positioned in the cardiac chamber to be displayed upon the interventional system and to be navigated in real-time over the registered 3D model. Preferably, the method and system also includes a storage medium to store the 3D model and wherein the interventional system receives the stored 3D model to register with the real-time image of the cardiac chamber.

13 Claims, 7 Drawing Sheets

U.S. PATENT DOCUMENTS

| | | | |
|---|---|---|---|
| 5,353,795 A | 10/1994 | Souza et al. | 128/653.2 |
| 5,391,199 A | 2/1995 | Ben-Haim | 607/122 |
| 5,431,688 A | 7/1995 | Freeman | 607/10 |
| 5,515,849 A | 5/1996 | Murashita et al. | |
| 5,568,384 A | 10/1996 | Robb et al. | 364/419.13 |
| 5,738,096 A | 4/1998 | Ben-Haim | 128/653.1 |
| 5,752,522 A | 5/1998 | Murphy | 600/587 |
| 5,765,561 A | 6/1998 | Chen et al. | |
| 5,823,958 A | 10/1998 | Truppe | 600/426 |
| 5,839,440 A | 11/1998 | Liou et al. | 128/654 |
| 5,951,475 A | 9/1999 | Gueziec et al. | 600/425 |
| 6,058,218 A | 5/2000 | Cline | |
| 6,081,577 A | 6/2000 | Webber | 378/23 |
| 6,154,516 A | 11/2000 | Heuscher et al. | 378/15 |
| 6,208,347 B1 | 3/2001 | Migdal | 345/419 |
| 6,233,304 B1 | 5/2001 | Hu et al. | 378/8 |
| 6,235,038 B1 | 5/2001 | Hunter et al. | 606/130 |
| 6,246,898 B1 | 6/2001 | Vesely | 600/424 |
| 6,249,693 B1 | 6/2001 | Cline et al. | 600/410 |
| 6,252,924 B1 | 6/2001 | Davantes et al. | 378/8 |
| 6,256,368 B1 | 7/2001 | Hsieh et al. | 378/8 |
| 6,266,553 B1 | 7/2001 | Fluhrer et al. | 600/428 |
| 6,289,115 B1 | 9/2001 | Takeo | 382/130 |
| 6,289,239 B1 | 9/2001 | Panescu et al. | 600/523 |
| 6,298,259 B1 | 10/2001 | Kucharczyk et al. | 600/411 |
| 6,314,310 B1 | 11/2001 | Ben-Haim et al. | 600/424 |
| 6,325,797 B1 | 12/2001 | Stewart et al. | 606/41 |
| 6,348,793 B1 | 2/2002 | Balloni et al. | 324/309 |
| 6,353,445 B1 | 3/2002 | Babula et al. | 345/733 |
| 6,381,485 B1 | 4/2002 | Hunter et al. | 600/407 |
| 6,389,104 B1 | 5/2002 | Bani-Hashemi et al. | 378/98.12 |
| 6,411,848 B2 | 6/2002 | Kramer et al. | 607/9 |
| 6,421,412 B1 | 7/2002 | Hsieh et al. | 378/9 |
| 6,456,867 B2 | 9/2002 | Reisfeld | 600/407 |
| 6,468,265 B1 | 10/2002 | Evans et al. | 606/1 |
| 6,490,475 B1 | 12/2002 | Seeley et al. | 600/426 |
| 6,490,479 B2 | 12/2002 | Bock | 600/518 |
| 6,504,894 B2 | 1/2003 | Pan | 378/8 |
| 6,522,906 B1 | 2/2003 | Salisbury, Jr. et al. | |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1 | 11/2003 | Keidar | 600/424 |
| 6,782,284 B1 | 8/2004 | Subramanyan et al. | 600/407 |
| 6,950,689 B1 | 9/2005 | Willis et al. | |
| 7,047,060 B1 | 5/2006 | Wu | |
| 7,286,866 B2 * | 10/2007 | Okerlund et al. | 600/407 |
| 7,346,381 B2 * | 3/2008 | Okerlund et al. | 600/407 |
| 2002/0010392 A1 | 1/2002 | Desai | 600/374 |
| 2002/0042570 A1 | 4/2002 | Schaldach et al. | |
| 2002/0046756 A1 | 4/2002 | Laizzo et al. | 128/899 |
| 2002/0138105 A1 | 9/2002 | Kralik | 607/9 |
| 2003/0018251 A1 | 1/2003 | Solomon | 600/427 |
| 2003/0023266 A1 | 1/2003 | Borillo et al. | 606/200 |
| 2003/0028183 A1 | 2/2003 | Sanchez et al. | 606/34 |
| 2003/0065260 A1 | 4/2003 | Cheng et al. | 600/427 |
| 2003/0097219 A1 | 5/2003 | O'Donnell et al. | 702/19 |
| 2003/0120264 A1 | 6/2003 | Lattouf | |
| 2003/0187358 A1 | 10/2003 | Okerlund et al. | 600/443 |
| 2003/0208116 A1 | 11/2003 | Liang et al. | |
| 2003/0220557 A1 | 11/2003 | Cleary et al. | 600/409 |
| 2004/0019274 A1 | 1/2004 | Galloway, Jr. et al. | |
| 2004/0027347 A1 | 2/2004 | Farsaie | 345/419 |
| 2004/0082846 A1 | 4/2004 | Johnson et al. | |
| 2004/0087850 A1 | 5/2004 | Okerlund et al. | 600/407 |
| 2004/0225212 A1 | 11/2004 | Okerlund et al. | 600/407 |
| 2004/0225328 A1 | 11/2004 | Okerlund et al. | 607/9 |
| 2004/0225331 A1 | 11/2004 | Okerlund et al. | 607/14 |

OTHER PUBLICATIONS

L. Gepstein et al., "A Novel Method for Nonfluoroscopic Catheter-Based Electroanatomical Mapping of the Heart: In Vitro and In Vivo Accuracy Results;" *Circulation* 1997; 95:1611-22.

S. Shpun et al., "Guidance of Radiofrequency Endocardial Ablation with Real-time Three-dimensional Magnetic Navigation System;" *Circulation* 1997; 96:2016-21.

J. Sra et al., "Electroanatomic Mapping to Identify Breakthrough Sites in Recurrent Typical Human Flutter;" *Paceing Clin. Electrophysiol* 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Rhythm;" *Circulation* 1998; 98:997-98.

C. C. Gomick et al., "Validation of a New Noncontact Catheter System for Electroanatomic Mapping of Left Ventricular Endocardium;" *Circulation* 1999; 99:829-835.

J. Sra et al., "Noncontact Mapping for Radiofrequency Ablation of Complex Cardiac Arrhythmias;" *J. Interven. Cardiac Electrophysiol* 2001; 5:323-331.

N. M.S. de Groot et al., "Three-Dimensional Catheter Positioning During Radiofrequency Ablation in Patients: First Application of a Real-Time Position Management System;" *J. Interven. Cardiac Electrophysiol* 2001; Nov. 11(11):1183-92.

J. Schreieck et al., "Radiofrequency Ablation of Cardiac Arrhythmias Using a Three-Dimensional Real-Time Position Management and Mapping System;" *Pacing Clin. Ekectrophysiol*, Dec. 2002, 25(12):1699-707.

F. Wittkampf et al., "Real-Time, Three-Dimensional, Nonfluoroscopic Localization of the Lasso Catheter;" *J. Interven. Cardiac Electrophysioll* 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven. Cardiac Electrophysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*; 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N. Engl. J. Med.* 2001; 344:873-880.

M.V. Pitzalis et al., "Cardiac Resynchronization Therapy Tailored by Echocardiographic Evaluation of Ventricular Acnchrony;" *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;"J. Am. Coll. Cardiol 2001; 38:1-47.

D. R. Ney "Volumetric Rendering of Computed Tomography Data: Principles and Techniques;" *IEEE Computer Graphics and Applications*; 1990; 24-32.

N. M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quaility Considerations;" *Computed Body Tomography*, 1998, Lippincot-Raven, Philadelphia, PA pp. 1-20.

W. M. Feinberg et al.; "Prevalence, Age Distribution, and Gender of Patients with Atrial Fibrillation;" *Arch. Intern. Med.* vol. 155; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology- Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, issue 20, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

PCT Search Report for PCT/US2004/020909.

F. H. M Wittkampf et al.; "LocaLisa: New Technique for Real-Time 3-Dimensional Localization of Regular Intracardiac Electrodes;" *Circulation*, 1999, 99:1312-1317.

"Advanced Vessel Analysis" product descritpoin, [online] http://www.gehealthcare.com/usen/ct/clin_app/products/aswessel.html [retrieved Dec. 1, 2004].

"CardilQ" product description, [online], http://egems.gehealtcare.com/geCommunity/Europe/flex_trial/awFlexTrial/aw3_1/eflextrial [retrieved Dec. 1, 2004].

Sra et al., "Registration of Three-Dimensional Left Atrial Computed Tomographic Images With Projection Images Obtained Using Fluoroscopy", Circulation 2005; 112: 3763-3768.

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

* cited by examiner

Immersible View of CS Origin from within the Right Atrium

Immersible view within CS near intersection of CS and circumflex

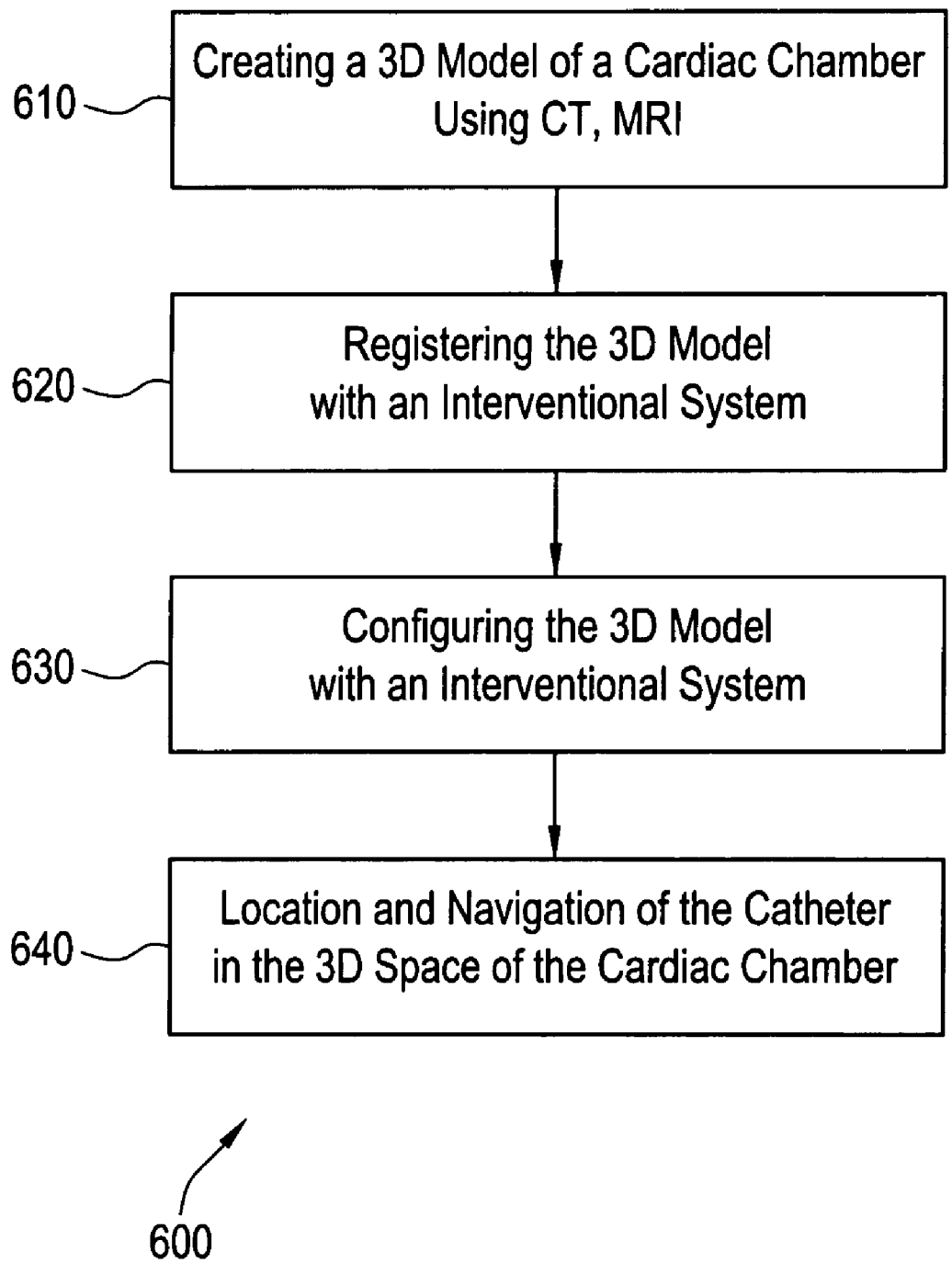

METHOD AND APPARATUS FOR MEDICAL INTERVENTION PROCEDURE PLANNING AND LOCATION AND NAVIGATION OF AN INTERVENTION TOOL

CROSS REFERENCE TO RELATED APPLICATIONS

The present application is a continuation-in-part of assigned U.S. patent application, Ser. No. 10/065,595 filed Nov. 1, 2002, the contents of which are incorporated herein by reference thereto which claims the benefit of U.S. Provisional Application Ser. No. 60/385,749, filed Jun. 4, 2002, which is incorporated by reference in its entirety. The present application also claims the benefit of U.S. Provisional Application No. 60/494,607, filed Aug. 12, 2003, the contents of which are incorporated by reference herein in their entirety.

BACKGROUND OF THE INVENTION

This invention relates generally to an imaging system, and more particularly to a method and apparatus for use of the imaging system in medical intervention procedure planning and location and navigation of an intervention tool.

Medical diagnostic and imaging systems are present in modern health care facilities. Such systems provide invaluable tools for identifying, diagnosing and treating physical conditions and greatly reduce the need for surgical diagnostic intervention. In many instances, final diagnosis and treatment proceed only after an attending physician or radiologist has complemented conventional examinations with detailed images of relevant areas and tissues via one or more imaging modalities.

Medical diagnosis and treatment can also be performed by using an interventional procedure such as congestive heart failure (CHF) intervention. It is estimated that approximately 6-7 million people in the United States and Europe have CHF. Some patients with CHF also experience left bundle branch block (LBBB), which negatively impacts the electrical conduction system of the heart. In patients with CHF and LBBB, delayed left ventricular ejection results from delayed ventricular depolarization, and in the presence of LBBB, ventricular contraction is asymmetrical, which causes ineffective contraction of the left ventricle. Cardiac resynchronization therapy, where both the right ventricle (RV) and left ventricle (LV) are paced simultaneously, has been shown to be effective in improving symptoms in patients with CHF and LBBB. One current clinical treatment for this condition is interventional bi-ventricular pacing, which involves: positioning RV and right atrial (RA) leads, positioning a sheath in the coronary sinus (CS), performing a CS angiogram to delineate a suitable branch for the LV lead placement, placing the lead for LV pacing in the posterior or lateral branches of the CS, and applying pacing signals to the RV and LV leads to simultaneously pace the RV and LV for synchronization.

Interventional bi-ventricular pacing therapy may involve a lengthy procedure, may result in unsuccessful lead placement in the CS due to the CS anatomy, or the lead itself may dislodge from the CS. In most cases, these situations are identified only at the time of the interventional procedure, resulting in abandonment of the procedure or the scheduling of a second procedure where, using a surgical incision, the LV lead is placed epicardially.

BRIEF DESCRIPTION OF THE INVENTION

In one embodiment, an imaging system for use in medical intervention procedure planning includes a medical scanner system for generating a volume of cardiac image data, a data acquisition system for acquiring the volume of cardiac image data, an image generation system for generating a viewable image from the volume of cardiac image data, a database for storing information from the data acquisition and image generation systems, an operator interface system for managing the medical scanner system, the data acquisition system, the image generation system, and the database, and a post-processing system for analyzing the volume of cardiac image data and displaying the viewable image and being responsive to the operator interface system. The operator interface system includes instructions for using the volume of cardiac image data and the viewable image for bi-ventricular pacing planning, atrial fibrillation procedure planning, or atrial flutter procedure planning.

In another embodiment, a computer system for use in a medical intervention procedure includes a data port for receiving probe information from the medical intervention procedure, a database for storing information acquired from an interventional procedure planning session, a memory comprising instructions for managing the probe information received at the data port and the stored information in the database, a processor for analyzing the information at the data port in combination with the stored information in the database, an operator interface system for managing the memory and the processor, and a display responsive to the operator interface for visualizing the information in the database in combination with the information at the data port.

In a further embodiment, a method for generating an image for use in medical intervention procedure planning includes acquiring a volume of cardiac image data from a medical scanner, managing the volume of cardiac image data through segmentation, processing the cardiac image data for viewing, viewing the cardiac image data in a viewable image, inserting a geometric marker into the volume of cardiac image data at an anatomical landmark for subsequent visualization, analysis and registration, selecting a viewable parameter in response to the geometric marker at the anatomical landmark, and saving a viewable image, an anatomical landmark, or a measured viewable parameter, in an image database.

In another embodiment, a method for using a volume of cardiac image data during a medical interventional procedure includes retrieving a procedure planning image from an image database, viewing the procedure planning image, applying a probe into a vessel of a patient during the interventional procedure, identifying a landmark of the probed vessel from the interventional procedure, registering the coordinate system of the interventional procedure with the coordinate system of the procedure planning image, and displaying the procedure planning image in response to the position of the applied probe for performing a real-time vessel tracking procedure on the probed vessel.

In still another embodiment, a method for using a volume of cardiac image data during a medical interventional procedure includes retrieving at least three distinct coordinates of the cardiac chamber and aligning the three distinct coordinates with the same coordinates used in an interventional system, such that the orientation of the cardiac chamber on the interventional system is similar to its original orientation at the time of imaging. In this manner, the interventional system uses the pre-stored 3D images to guide an interventional tool, such as a catheter, for example in real-time.

In yet another embodiment, a fluoroscopy or other interventional system is configured such that an interventional tool such as a mapping-ablation catheter, for example, is located and tracked in real-time as it is navigated in the 3D space of the cardiac chamber.

BRIEF DESCRIPTION OF THE DRAWINGS

Referring now to the figures, which are exemplary embodiments, and wherein like elements are numbered alike:

FIG. 7 is a flowchart of a process for using the method and apparatus of an embodiment of the invention during location and navigation of a mapping and ablation catheter in a cardiac chamber.

DETAILED DESCRIPTION OF THE INVENTION

Figure 1:
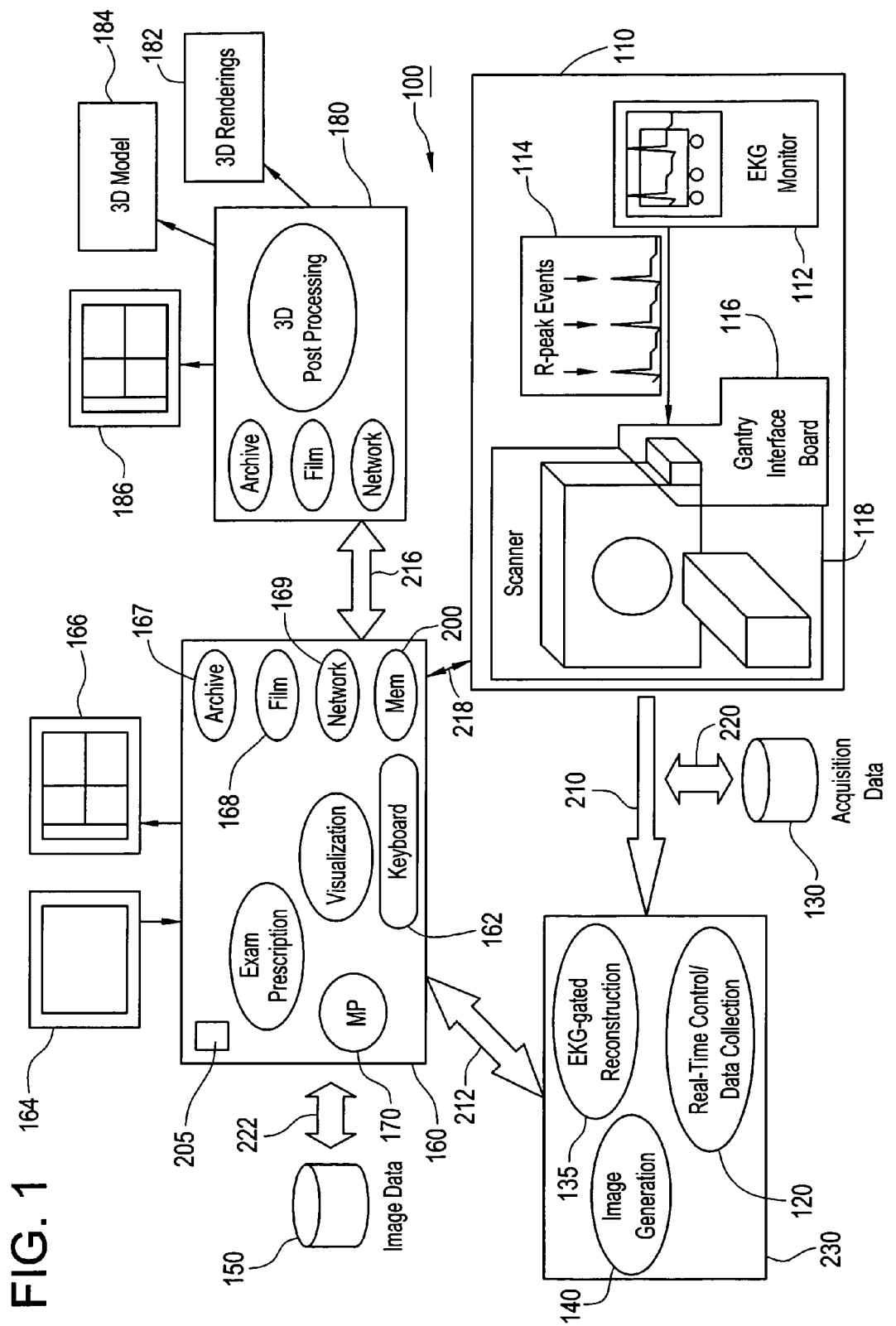
FIG. 1 depicts a generalized schematic of an imaging system for use in medical intervention procedure planning.
Figure 2:
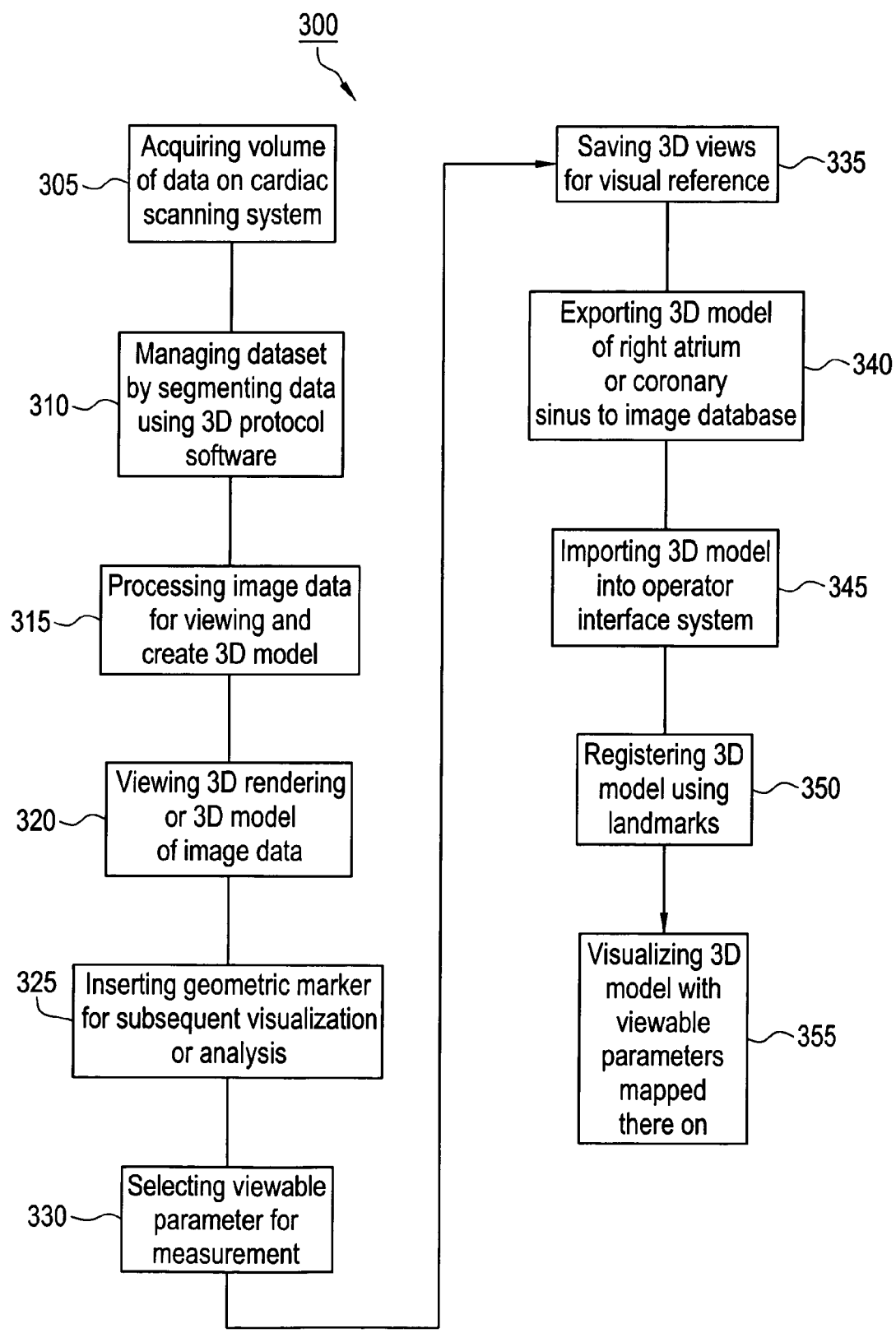
FIG. 2 depicts a generalized flowchart of a process for implementing an embodiment of the invention using the imaging system of FIG. 1.
Figure 3:
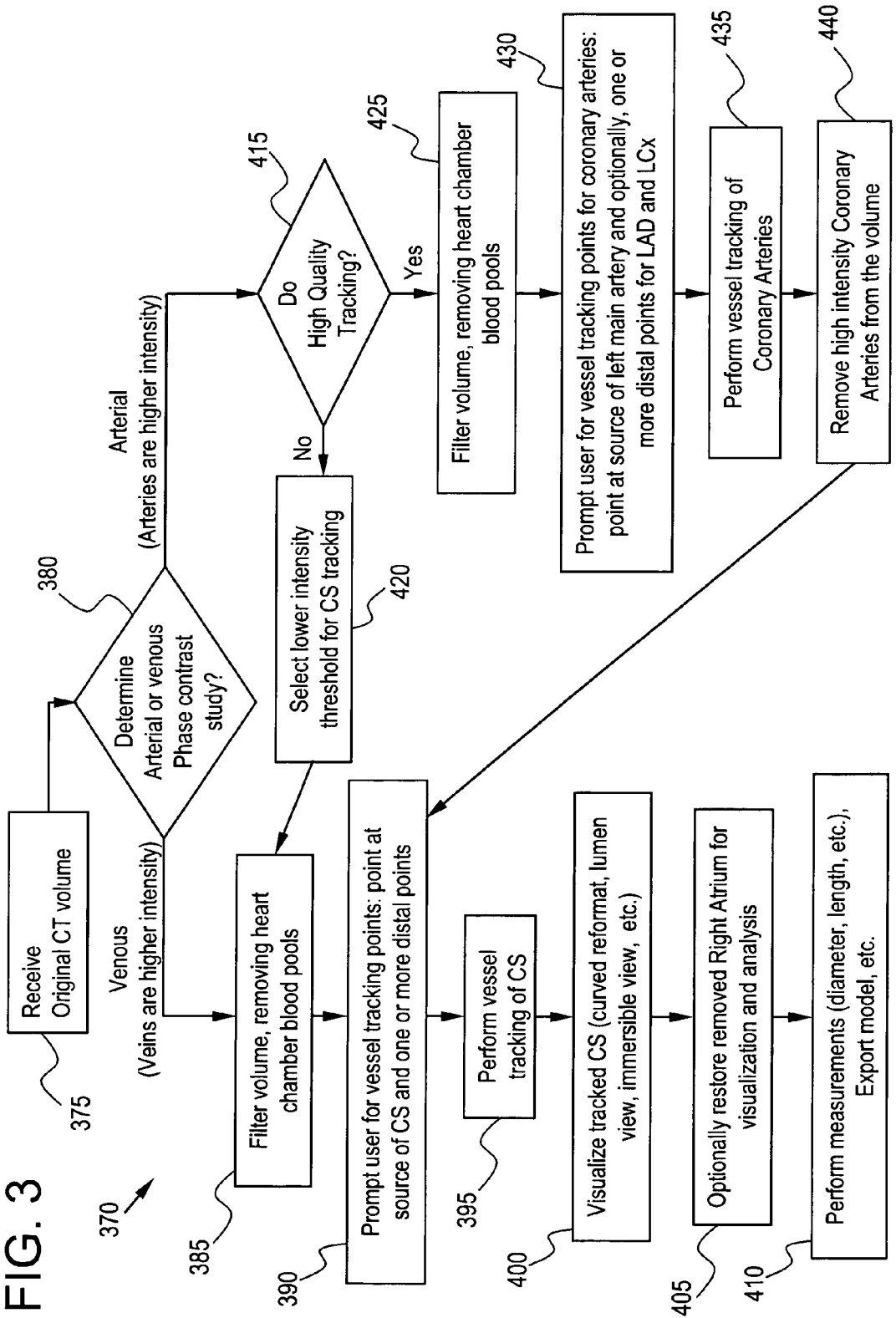
FIG. 3 depicts a flowchart of a process for automatically establishing the dynamic segmentation threshold value for vessel tracking of the coronary sinus for both arterial and venous-phase contrast-enhanced studies in accordance with an embodiment of the invention.

A detailed description of an embodiment of the invention is presented herein by way of exemplification and not limitation with reference to FIGS. 1-3.

FIG. 1 depicts a generalized schematic of an imaging system 100 for use in medical intervention procedure planning, such as, for example, bi-ventricular procedure planning, atrial fibrillation procedure planning, or atrial flutter procedure planning. The imaging system 100 includes: a medical scanner system 110 for generating cardiac image data, such as, for example, image data of the left atrium, the left ventricle, the right atrium and the coronary sinus, a data acquisition system 120 for acquiring the cardiac image data from medical scanner system 110, an acquisition database 130 for storing the cardiac image data from data acquisition system 120, an image generation system 140 for generating a viewable image from the cardiac image data stored in acquisition database 130, an image database 150 for storing the viewable image from image generation system 140, an operator interface system 160 for managing the medical scanner system 110 and the cardiac image data and viewable image in databases 130, 150, which may be combined into one database, and a post-processing system 180 for analyzing and displaying the viewable image in database 150 and being responsive to operator interface system 160. Post-processing software in post-processing system 180 includes instructions, and is therefore adapted, to analyze data and display images, thereby converting post-processing system 180 from a general post-processor into a specialized post-processor. Scanned data that is capable of being converted into a viewable image is referred to herein as image data.

System communication links 210, 212, 216, 218 and database communication links 220, 222 provide a means for signal communication amongst and between systems 110, 120, 140, 160, 180 and databases 130, 150. Communication links 210-222 may be hardwired or wireless. Operator interface system 160 may be a standalone input/output terminal or a computer including instructions in a variety of computer languages for use on a variety of computer platforms, such as, for example, DOS™-based computer systems, Apple™-based computer systems, Windows™-based computer systems, HTML-based computer systems, or the like.

Operator interface system 160 includes a processor 170, such as, for example, a microprocessor, for managing the medical scanner system 110, for managing the data acquisition and image generation systems 120, 140, for processing and managing the information in acquisition and image databases 130, 150, and for managing the post-processing at post-processing system 180. Operator interface system 160 also includes: a memory 200 that contains specific instructions relating to a cardiac bi-ventricular pacing planning procedure, user input means, such as, for example, a keyboard 162, and user output means, such as, for example, displays 164, 166. Display 164 may be adapted for exam prescription, and display 166 may be adapted for visualization. Alternatively, displays 164 and 166 may be integrated into one display. Exam prescription includes such input parameters as: scan or region of scan definition, data acquisition control, scanner image control, and the like. Operator interface system 160 may also be employed during an actual interventional procedure to display both interventional procedure planning images and interventional procedure real-time images, as discussed below. During an actual medical interventional procedure, data port 205 accepts information from a medical probe, such as, for example, a catheter, thereby permitting interventional procedure planning data to be analyzed in a real-time fashion during the actual interventional procedure.

Medical scanner system 110 includes an electrocardiogram (EKG) monitor 112 that outputs R-peak events 114, which generally delineate the beginning of a heart cycle, through an interface board 116 into a scanner 118. The interface board 116 enables synchronization between the scanner data and the EKG monitor data. Alternatively, the interface board 116 may be used to couple the EKG monitor 112 to the scanner 118. An example of an interface board 116 is a Gantry interface board. The exemplary scanner 118 is a cardiac computed tomography (CT) system with support for cardiac imaging, however, the illustrated scanner 118 is for exemplary purposes only; other imaging systems known in the art may also be used. Examples of other imaging systems include, but are not limited to, X-ray systems (including both conventional and digital or digitized imaging systems), magnetic resonance (MR) systems, positron emission tomography (PET) systems, ultrasound systems, nuclear medicine systems, and 3D fluoroscopy systems. Medical scanner system 110 also includes EKG gated acquisition or image reconstruction 135 capabilities to image the heart free of motion, typically in its diastolic phase. Medical scanner system 110 further includes circuitry for acquiring image data and for transforming the data into a useable form which is then processed to create a reconstructed image of features of interest within the patient. The image data acquisition and processing circuitry is often referred to as a "scanner", regardless of the type of imaging system, because some sort of physical or electronic scanning often occurs in the imaging process. The particular components of the system and related circuitry differ greatly between imaging systems due to the different physics and data processing requirements of the different system. However, it will be appreciated that the present invention can be applied regardless of the selection of a particular imaging system. For example, although EKG gated datasets have been described above, it is not limited to EKG gated datasets, as it may apply to respiratory gated datasets, for example, in another imaging modality.

Data is output from scanner 118 into subsystem 230 that includes software to perform data acquisition in data acquisition system 120, and image generation in image generation system 140. Data control is either provided by operator interface system 160 or within subsystem 230 via communication link 212. Data that is output from the scanner 118, including R-peak events 114, is stored in the acquisition database 130. Data acquisition in system 120 is performed according to one or more acquisition protocols that are optimized for imaging the heart, and specifically for imaging the right atrium and/or coronary sinus. Image generation in system 140 is performed using one or more optimized 3D protocols for automated image segmentation of the CT image dataset, thereby providing an image of the inner surface of the right atrium and/or coronary sinus.

Image data from image generation system 140 is communicated via link 212 to operator interface system 160. The image data used by software at operator interface system 160 for exam prescription and visualization is stored in image database 150. The image data may be archived 167, put on film 168 or sent over a network 169 to post-processing system 180 for analysis and review, including 3D post-processing. Post-processing system (180) may not be a stand-alone system, as post processing may optionally be performed on the operator interface system (160), for example. The post-processing software used in post-processing system 180 performs segmentation of cardiac image volume data to extract relevant substructures such as the right atrium and coronary sinus vessel, defining a subvolume or 3D model of the substructure. The post-processing software also provides 3D renderings, including immersible (or navigator) views, that is, visualization from the inside, of the right atrium and coronary sinus. These special views can be saved in a 3D rendering file 182, and a geometric model of these structures and substructures can be saved to a 3D model file 184, which are saved in image database 150, and may be viewed by the operator of operator interface system 160 during either the medical planning of the intervention procedure or during the interventional procedure itself, such as in combination with a projection image during a 3D-fluoroscopy procedure, which is alternatively referred to as an interventional image. In the case of the coronary sinus, the inner vessel surface is clearly defined in 3D rendering 182 and 3D model 184. The 3D model 184 may include anatomical, or geometric, landmarks, such as, for example, the right atrium, coronary sinus, or thebesian valve, that can be used for 3D registration of the 3D model 184 with the coordinate system of the respective anatomical structures viewed on the operator interface system 160 during an interventional procedure, thereby enabling concurrent use of the 3D model 184 during a subsequent interventional procedure, such as with a projection image during a 3D-fluoroscopy procedure. The coordinate system relating to the anatomical structures as viewed during an interventional procedure is referred to as the interventional coordinate system. The 3D model 184 can be exported in one of several formats: a wire mesh geometric model; a solid geometric model; a set of contours associated with each image slice; a segmented volume of binary images; a run-length encoded binary segmentation mask (wherein a segmentation mask is representative of the location of voxels of interest); or a medical digital imaging object using a radiation therapy (RT) object standard or similar object. Other formats known in the art can also be used to store and export the 3D models 184. Additionally, the operator can view the 3D rendering and model 182, 184 on a display 186. The 3D renderings can contain 3D camera information (3D position, view angles, and view-up vector, for example) which specify how the interventional system can render the 3D model at the same orientation. In another embodiment, the operator interface system 160 could contain the functions of the post-processor system 180. In yet another embodiment, display 186 may be integrated with displays 164 and 166.

The software of post-processing system 180 includes analytical methods for performing vessel tracking, which provides the user of operator interface system 160 with the capability of analyzing and viewing various parameters of the coronary sinus, or another vessel of interest, which include: the diameter and path length of the vessel or vessel segment, the significant branches of the vessel, the degree of curvature (the degree of bend) of the vessel, and the degree of obstruction within the vessel. The ability to perform vessel tracking according to an embodiment of the invention provides the operator with the capability of performing an analytical examination during the bi-ventricular pacing planning procedure without physically entering an analytical probe into the patient's body. The post-processing software also employs known 3D model manipulation techniques, such as rotation and isometric viewing, to enable the operator to visualize the 3D model, of the CS or its branches for example, in different planes, such as cross section views (where the plane is normal to a direction vector positioned on the center-line of the vessel) and longitudinal section views (where plane in parallel to and includes a segment of the vessel). The post-processing software also provides "warped" views of the CS that include a curved reformat view (where the vessel tracking information is projected onto a single view) and a "lumen view" (where the vessel is straightened and displayed in one plane for measurement/analysis purposes). The vessel tracking post-processing software also includes the capability of placing a geometric marker at the centerline of the CS and performing vectorial tracking through the vessel along the vessel's centerline.

The post-processing software also includes an algorithm for automatically adjusting the dynamic segmentation threshold value used in vessel tracking segmentation such that the coronary sinus can be tracked for both arterial and venous-phase contrast-enhanced studies. Since the intensity of the voxels within the coronary sinus would be lower for images from an arterial phase data acquisition, due to the influence that blood has on the image intensity, the segmentation threshold value must be adjusted appropriately in order to obtain correct segmentation imaging. Image brightness is established prior to segmentation and in accordance with the presence of an arterial or venous-phase study. The capability of the post-processing software to automatically distinguish between the different image contrasts of an arterial or venous-phase study is referred to as contrast-enhanced segmentation analysis, as discussed in reference to FIG. 3 below.

Referring now to FIG. 2, a flowchart depicts an exemplary process 300 whereby image data created on a cardiac CT is used for medical intervention planning, and more specifically for bi-ventricular pacing planning. Exemplary process 300 may be employed in conjunction with the use of imaging system 100.

The process 300 begins at step 305 where a volume of data is acquired on the cardiac CT scanner 118 using a protocol that is optimized for the right atrium and/or coronary sinus. An example of a protocol that could be used is a vessel imaging protocol that uses a helical scan acquisition technique with gated reconstruction. In an exemplary embodiment, parameters used by the vessel imaging protocol could include 0.5 second Gantry periods with 0.275 helical pitch factors using single or multi-sector cardiac reconstruction. Parameters could also include 120 kilovolts, 250 milliamps, and 1.25 millimeters image thickness on a multi-slice CT scanner. The generation of a volume of data is accomplished by combining many sequential time slices of scanned data.

At step 310, management of the image dataset is accomplished by segmenting the data using post-processing software that includes a 3D protocol designed to extract data relating to the inner surface of the right atrium and/or coronary sinus. The segmentation of data from a dataset refers to the extraction of a specific portion of the dataset that relates to an anatomical landmark of interest, such as, for example, the right atrium, the coronary sinus, or an external anatomical marker (e.g., a marker external to the patient). Input from an operator, via an operator interface system 160 discussed in reference to FIG. 1, provides the necessary information as to whether the dataset should be managed in accordance with a right atrium or coronary sinus algorithm. In an exemplary embodiment, post processing software functions can include vessel tracking analysis and the selection of image brightness thresholds. The data management process at step 310 may require one or more queues from the operator, during which time the operator may be stepped through the process. These queues typically include, for example, depositing a point at the origin of the CS and at the distal end of each branch of the CS to facilitate vessel tracking. The 3D protocol includes default views for the scanned subject and default processing steps that can be performed on the image data, thereby providing an automated procedure for 3D segmentation, visualization, analysis, and exporting. Use of the automated process is managed at the operator interface system 160 where an operator selects the appropriate automated procedure to be followed, for example, whether the right atrium or coronary sinus is to be analyzed.

At step 315, processing of the image data for viewing is performed and a 3D model is created.

At step 320, the right atrium and/or coronary sinus is viewed or visualized using multiplanar volume reformat (MPVR), Maximum Intensity Projection (MIP), 3D surface rendering, or volume rendering (VR), which may include an immersible view (i.e., view from the inside). A variety of 3D software packages are available for cardiac volume analysis and cardiac image quality analysis.

At step 325, the operator inserts a geometric marker, such as, for example, a sphere, into the volume at an anatomical landmark for subsequent visualization or analysis. Multiple geometric markers and geometric landmarks may be inserted and visualized at one time. Geometric landmarks can be visualized in a different color scheme than the inner surface of an anatomical landmark, the coronary sinus, for example. Alternatively, geometric markers can be inserted into the volume at the geometric landmarks and the coronary sinus can be visualized in a translucent fashion with the geometric landmarks being viewed in an opaque fashion. Furthermore, different geometric markers can be used to identify different anatomical landmarks, thereby permitting multiple volumes to be rendered at different degrees of translucency. For example, a model of the heart may be rendered in a translucent fashion and a model of the CS may be rendered in an opaque fashion, thereby permitting the CS to be viewed in the context of the entire heart. A volume rendering tool such as the one described previously in reference to step 315 can be used to perform this step. In an exemplary embodiment of the invention, the operator will be stepped through the visualization and landmark identification procedure.

At step 330, the operator selects a viewable parameter to be measured or viewed, such as, for example, the diameter of the coronary sinus, the path length of the coronary sinus, the viewing of significant branches of the coronary sinus, the quantification of the curvature (the degree of bend) of the coronary sinus, and the quantification of the degree of obstruction, stenosis, within the coronary sinus, by selecting a geometric marking associated with an anatomical landmark inserted at step 325, whereby the post-processing software then calculates the selected parameter and provides a display of the measurement or view. Appropriate 3D renderings for this analysis includes curved reformat and lumen views.

At step 335, specific 3D models or renderings (3D views) that are requested for visual reference during the medical intervention planning procedure are saved. Such 3D views may include a viewable cardiac image, an anatomical landmark, or a measured viewable parameter. The 3D views could be saved in a variety of manners including industry standard medical digital imaging images, on film or in a multimedia format. These 3D views could also be blended with the projection image on a fluoroscopy system. A fluoroscopy system can include positioning an x-ray tube at a precise orientation with respect to the patient and a detector on the other side of the patient in order to get real-time x-ray images. The proper orientation is based on the 3D view angles determined during the post-processing analysis where the view angle orientation information is specified in the 3D renderings or in the 3D model itself. A fluoroscopy system is an example of one way to guide a catheter during a procedure.

At step 340, a 3D model of the right atrium and/or coronary sinus is exported using a format of choice to an image database. Possible formats include: a wire mesh geometric model; a solid geometric model; a series of contours associated with each image slice; a segmented volume of binary images; a run-length encoded binary segmentation mask; and a medical digital imaging object such as the radiation therapy medical digital imaging object being used under radiation therapy medical digital imaging industry standards. In an exemplary embodiment, all non-relevant data in the binary images are set to zero and the segmented volume of binary images includes only the non-zero information. The value of the voxels correspond to CT attenuation, and the density of a tissue expressed in Hounsfield units makes up the segmented volume of binary images. In another embodiment, a binary segmentation mask specifies the location of all relevant voxels within the original volume itself.

At step 345, the 3D model that has been exported is input into the operator interface system.

At step 350, the 3D model 184 is registered with the corresponding landmarks that were identified in step 325. The 3D model 184 can be registered in the coordinate system of the operator interface system using rigid or non-rigid registration techniques. A rigid registration technique typically requires the identification of at least three anatomical landmarks, whereas a non-rigid registration technique may require the identification of more than three anatomical landmarks. With rigid registration, the 3D model 184 can be translated or rotated during an interventional procedure to match up with located landmarks which are imaged or identified by the interventional system. Additional landmarks can also be used such that a transformation of best fit (in a mean squared error sense) is calculated. The centerline for vessel tracking, near the ostium of the CS for example, can also be used to facilitate the registration of the 3D model in the interventional system coordinate system. With non-rigid registration, the 3D model 184 can also be stretched and warped.

At step 355, the model is further visualized via the operator interface system and selected viewable parameters are mapped onto the model. The exemplary embodiment described above refers to one 3D model. However, this could be expanded to any number of 3D models being exported by the cardiac imaging system and imported into the operator interface system.

Referring now to FIG. 3, a flowchart of a process 370 for automatically establishing the dynamic segmentation threshold value for vessel tracking of the coronary sinus for both arterial and venous-phase contrast-enhanced studies in accordance with an embodiment of the invention is depicted. The algorithm of FIG. 3 is included in the post-processing software of post-processing system 180.

Process 370 begins at step 375, where the original procedure planning CT volume data (volume of cardiac image data) is received from image database 150. At step 380, it is determined, by either comparative measurement, image header information, or user input, whether an arterial or a venous-phase contrast-study is under review.

If a venous-phase contrast-study is under review, process logic passes to step 385, where the volume of data is first filtered to remove the heart chamber blood pools. At step 390, the user is prompted for vessel tracking points, such as, for example, a point at the source of the CS and one or more distal points. At step 395, the post-processing software performs a vessel tracking procedure on the CS using vessel tracking methods discussed herein. At step 400, the tracked CS is visualized using curved reformat, lumen view, or navigator view, for example. At step 405, the right atrium, previously removed in step 385, is optionally restored for further visualization and analysis. At step 410, measurements are performed on the vessel or vessel segment, and model data is exported as desired.

If at step 380, an arterial-phase contrast-study is under review, process logic passes to step 415, where it is determined, by user input, for example, whether high quality tracking is to be performed. If no high quality tracking is to be performed, process logic passes to step 420, where a low intensity threshold for CS tracking is selected. After step 420, process logic passes to the block of step 385 and continues as discussed above.

If at step 415, it is determined that high quality tracking is to be performed, process logic passes to step 425 where the volume of data is first filtered to remove the heart chamber blood pools. At step 430, the user is prompted for vessel tracking points for the coronary arteries, such as, for example, a point at the source of the left main artery and optionally one or more distal points for LAD and LCx. At step 435, the post-processing software performs a vessel tracking procedure on the coronary arteries using vessel tracking methods discussed herein. At step 440, the high intensity coronary arteries are removed from the volume. After step 440, process logic passes to the block of step 390 and continues as discussed above.

Figure 4:
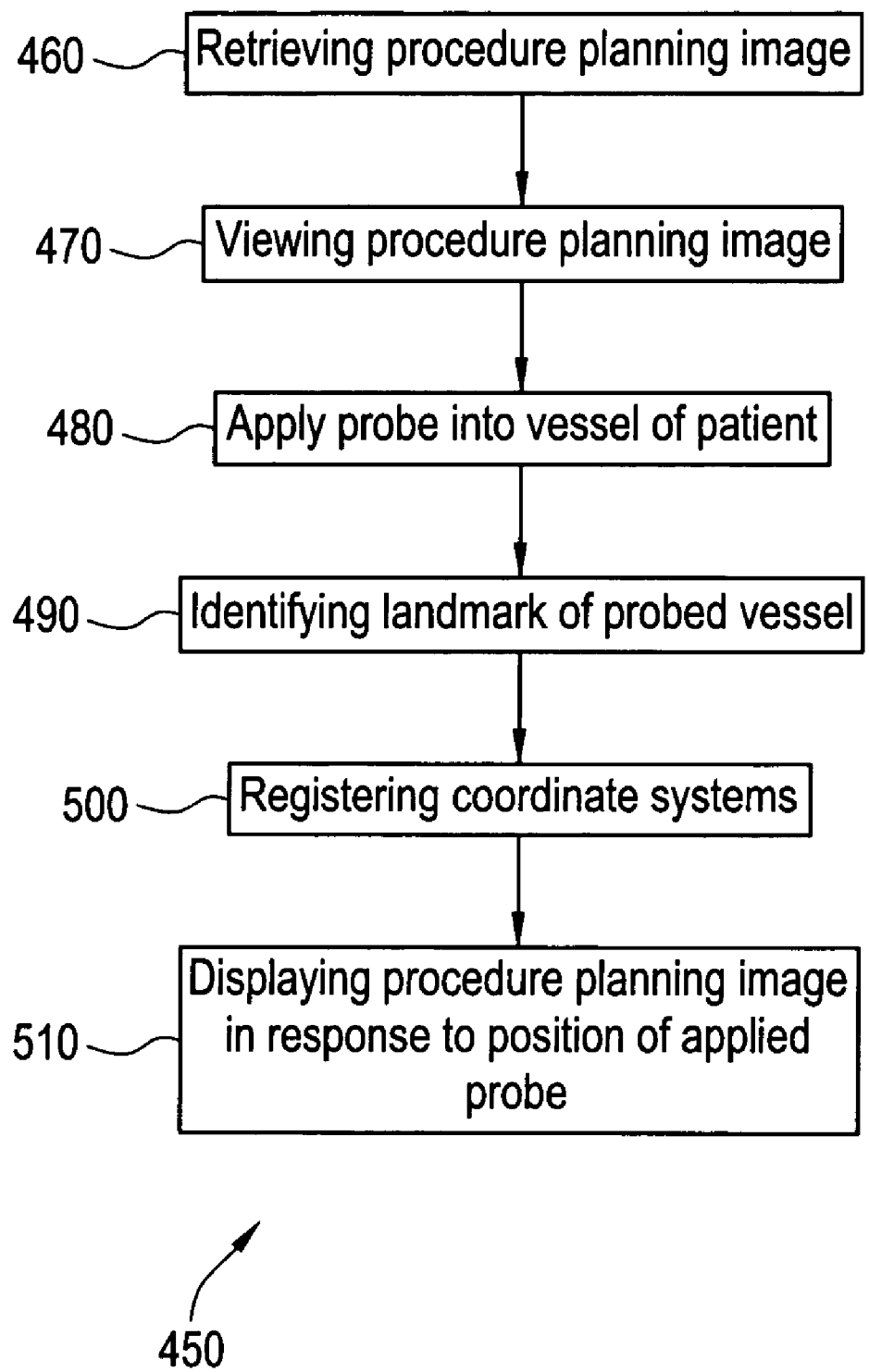
FIG. 4 depicts a flowchart of a process for using the method and apparatus of an embodiment of the invention during an intervention procedure.

As discussed above and shown generally in the flowchart 450 of FIG. 4, the volume of cardiac image data of a patient captured during an interventional planning procedure can be retrieved, displayed and used during an interventional procedure on the patient. During the interventional procedure, a probe, such as a catheter, is inserted into the coronary sinus of the patient and is used to control vessel tracking of the coronary sinus model. To accomplish this real-time vessel tracking, first, a volume of cardiac image data from the interventional planning procedure planning is retrieved 460 from the image database, and then segmented (to display the coronary sinus for example) and displayed 470. Next, a catheter is inserted 480 into the coronary sinus of the patient, and then a landmark, such as the origin of the coronary sinus, from the interventional procedure is identified 490, thereby permitting registration 500 of the two coordinate systems (i.e., the interventional procedure planning and the interventional procedure coordinate systems). Registration 500 includes centerline registration, where the centerline of a vessel, such as the CS, for example, may be used as a geometric landmark. After registration, the procedure planning image (immersion view of coronary sinus, for example) can be displayed 510 in response to the position of the applied probe, thereby permitting real-time vessel tracking of the coronary sinus. During the real-time vessel tracking intervention procedure, the location of the point of the catheter can also be displayed along with the procedure planning image, using immersible view, navigation view, volume rendering view, or any other view discussed herein, thereby facilitating real-time navigation through the vessel (for example, coronary sinus). The projection of the 3D image, including the current catheter location, can be projected onto, and combined with, the 3D fluoroscopy image at the same viewing angle.

FIG. 7 depicts a flowchart 600 of a method and system of location and navigation of a mapping ablation catheter in a 3D space of a cardiac chamber. Beginning at step 610, during imaging, a significant volume of data is acquired from the cardiac CT system using a protocol that is optimized for cardiac chambers. In the next step 620, the image dataset is segmented with post processing software using a 3D protocol designed to extract the area and chamber of interest. The obtained data and images are stored on a storage medium such that the data can be transferred to remote locations and utilized in the future. During the recording of the image, a plurality of reference points are recorded on the stored image, such that the coordinates of these reference points can be used in registering the stored image as described above. Typically, the method includes storing at least three reference points, although other amounts are contemplated. The endocardial views of the heart (views from inside) are also obtained.

In the next step 630, the stored 3D model of the cardiac chamber is transferred to the fluoroscopy system or a computer workstation of another interventional system.

The mode of transfer includes wireframe model, Dicom object or both. The interventional system aligns the stored coordinate system of the 3D image with the patient being examined such that the orientation of the transferred image is the same as during the real-time imaging.

As shown in the next step 640, the interventional system is then configured to locate and navigate the mapping ablation catheter. As indicated in this step, the location of the catheter can also be seen over the navigator views of the cardiac chamber. It will be noted that although an ablation catheter is illustrated as be located and navigated, any interventional tool is contemplated, including a biventricular lead, for example.

Figure 5:
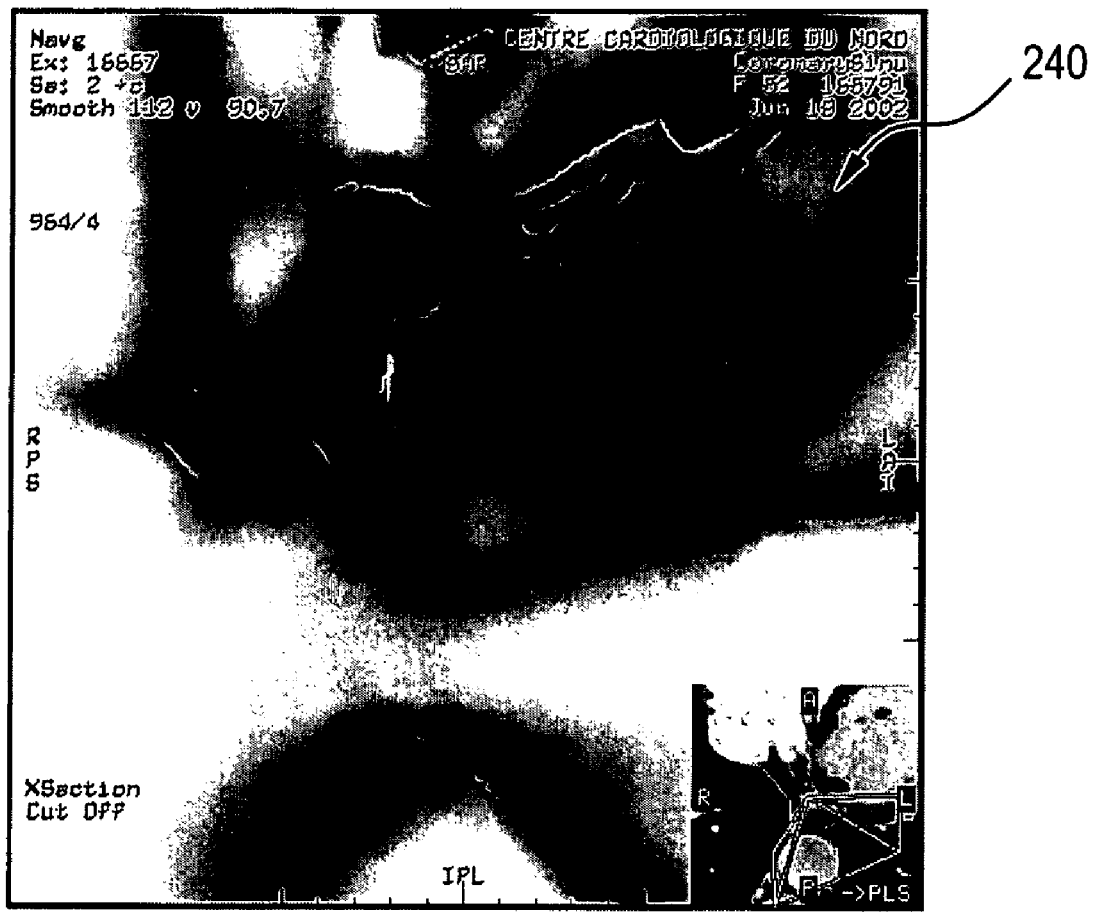
FIG. 5 depicts an immersible view of the coronary sinus origin from within the right atrium generated in accordance with an embodiment of the invention.
Figure 6:
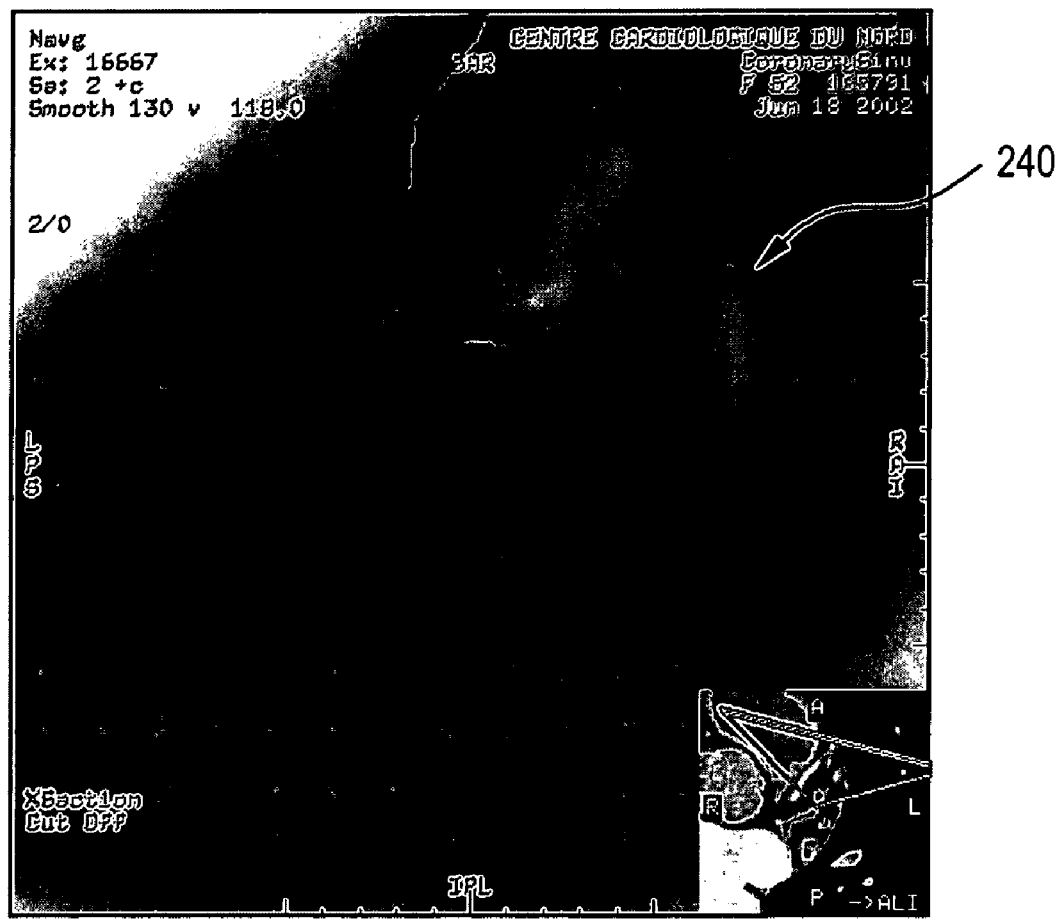
FIG. 6 depicts an immersible view within the coronary sinus near the intersection of the coronary sinus and the circumflex generated in accordance with an embodiment of the invention.

Referring now to FIGS. 5 and 6, a navigator view of the origin of the CS 240 from within the RA and a navigator view within the CS 240 near the intersection of the CS and the circumflex are shown, respectively. FIGS. 5 and 6 represent only two instances of a plurality of images created during a vessel tracking analysis and were generated in accordance with an embodiment of the invention in the following manner. Using the imaging system 100 of FIG. 1, a volume of cardiac image data was acquired 305 by medical scanner system 110 using the acquisition protocol discussed below. The image data was then segmented 310 to extract out the CS 240 and then processed 315 for 3D model creation and viewing. Vessel tracking of the CS 240 was accomplished in accordance with the process of FIG. 3, which delineates the steps necessary for appropriate vessel tracking depending on whether a venous-phase or arterial-phase contrast-enhanced study is being analyzed. The resulting vessel tracking images, two depicted in FIGS. 5 and 6, provide the operator, or physician, with a medical tool that enables viewing of the patient's actual cardiac anatomy for use during cardiac procedure planning.

In reference to FIGS. 5 and 6, a cardiac helical acquisition was used with retrospectively EKG-gated reconstruction on a 4/8/16/32+ detector row multi-slice scanner. Example scanner parameters were set at 120 kv, 350 mA, 0.5 sec rotation period, 0.3 helical pitch factor, 1.25 or 0.625 mm slice thickness, with segmented reconstruction at 75% cardiac phase location. Scan orientation was primarily from the bottom of the heart towards the top in order to acquire the more critical data early in the acquisition (considering patient motion, breathing, for example). Prior to the cardiac helical scan, a timing bolus acquisition was performed to determine the optimal preparation delay (the time between the beginning of contrast injection and the start of the cardiac helical scan). Following the scan and reconstruction of the cardiac images, and where motion artifacts were seen in the images, a multiphase reconstruction was prescribed over the full heart cycle. Phase location was selected at around 45% when the patient experienced arrhythmia during the scan. Multi-sector reconstruction may be employed where motion artifacts were still seen. The selection of a multi-sector reconstruction procedure may be facilitated using a multiphase post processing 3D viewer. The most optimal set of images (best phase, best reconstruction type, for example) were selected, and then post processing segmentation was performed as defined by the specific 3D protocol for the anatomical landmark under study (the right atrium, coronary sinus, for example).

Alternatively, two other options are available for acquisition. First, prospectively gated cine acquisitions may be used, or second, a relaxed cardiac gated reconstruction technique (using a phase location tolerance of +/−10% for example) with cardiac gated helical scanning, such that helical pitch is greater than that of standard cardiac acquisition. Both alternative approaches allow for less radiation dose to the patient but may affect image quality due to arrhythmia, for example.

Through bi-ventricular pacing planning in accordance with an embodiment of the invention, interventional bi-ventricular pacing therapy can be planned out ahead of the actual interventional procedure, and the images obtained during the planning procedure can be used during the actual interventional procedure. By providing the interventionalist with knowledge of the CS anatomy before intervention, an appropriate interventional procedure suitable for the particular patient can be identified, thereby improving the efficacy of the interventional procedure.

The 3D model can also be used for left ventricle (LV) lead placement during the interventional procedure. Once the 3D model of the CS has been registered within the interventional system coordinate system, the system can provide real-time navigation of the LV lead to the appropriate branch of the CS using 3D and immersible (navigator-like) views of the model and the real-time location of the LV lead during the placement procedure. In a real-time navigation procedure, the vessel tracking images, two instances depicted in FIGS. 5 and 6, are viewed in response to the probe, or catheter, being maneuvered during the interventional procedure. It will be appreciated that the present invention is not limited to the analysis of the CS but is also applicable to other volumes of cardiac image data. Furthermore, the present invention is not limited to cardiac chambers, as non cardiac datasets of other anatomy are envisioned.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An imaging system for use in medical intervention procedure planning, comprising:
   a medical scanner system configured for generating a volume of cardiac image data;
   a data acquisition system configured for acquiring the volume of cardiac image data;
   an image generation system configured for generating at least one viewable image from the volume of cardiac image data;
   a database configured for storing information from said data acquisition and image generation systems;
   an operator interface system configured for managing at least one of said medical scanner system, said data acquisition system, said image generation system, and said database;
   a post-processing system configured for analyzing the volume of cardiac image data and displaying the at least one viewable image and being responsive to said operator interface system, said post-processing system is further adapted to insert at least three geometric markers for subsequent visualization, analysis and registration, each of said three geometric markers corresponding with anatomical landmarks in the volume of cardiac image data, for use in the location and navigation of an interventional tool;
   wherein said operator interface system comprises computer executable instructions stored in a memory for using the volume of cardiac image data and the at least one viewable image in at least one of a bi-ventricular pacing planning, an atrial fibrillation planning, and an atrial flutter planning procedure prior to an actual medical interventional procedure; and
   wherein said operator interface system comprises computer executable instructions stored in a memory for using the volume of cardiac image data and the at least one viewable image in location and navigation of an interventional tool in a 3D space of a cardiac chamber corresponding to the volume of cardiac image data.

2. The imaging system of claim 1, wherein said medical scanner system comprises at least one of a CT system, a MR system, an Ultrasound system, a 3D Fluoroscopy system, and a PET system.

3. The imaging system of claim 1, wherein said database includes storage for storing image data of at least one of a right atrium, a left atrium, a left ventricle, and a coronary sinus.

4. The imaging system of claim 1, wherein said database includes storage for storing the at least one viewable image of at least one of the right atrium and the coronary sinus.

5. The imaging system of claim 1, wherein said operator interface system includes instructions for segmenting the volume of cardiac image data for viewing at least one of a right atrium, a left atrium, a left ventricle, and a coronary sinus.

6. The imaging system of claim 5, wherein said operator interface system includes instructions for viewing the at least one viewable image in different planes.

7. The imaging system of claim 5, wherein said post-processing system includes instructions for performing vessel tracking of the coronary sinus from the volume of cardiac image data.

8. The imaging system of claim 7, wherein said instructions further include instructions for performing vectorial vessel tracking along the centerline of the viewable image of the coronary sinus.

9. The imaging system of claim 1, wherein:
said post-processing system is adapted to display the at least one viewable image in at least one of a three-dimensional surface rendering, a three-dimensional inner surface rendering, a three-dimensional volume rendering, a three-dimensional segmented model view, MPVR, MIP, curved reformat, lumen view, and an immersible view;
said post-processing system is further adapted to display a viewable image of at least one of the heart, a coronary sinus, a left ventricle, a left atrium, and a right atrium; and,
said post-processing system is further adapted to display a first image of at least one of the heart, coronary sinus, left ventricle, left atrium, and right atrium in one of a translucent fashion and an opaque fashion while a second image of the coronary sinus is displayed in one of the translucent fashion and opaque fashion opposite the first image.

10. An imaging system for use in medical intervention procedure planning, comprising:
a medical scanner system configured for generating a volume of cardiac image data;
a data acquisition system configured for acquiring the volume of cardiac image data;
an image generation system configured for generating at least one viewable image from the volume of cardiac image data;
a database configured for storing information from said data acquisition and image generation systems;
an operator interface system configured for managing at least one of said medical scanner system, said data acquisition system, said image generation system, and said database;
a post-processing system configured for analyzing the volume of cardiac image data and displaying the at least one viewable image and being responsive to said operator interface system;
wherein said operator interface system comprises computer executable instructions stored in a memory for using the volume of cardiac image data and the at least one viewable image in at least one of a bi-ventricular pacing planning, an atrial fibrillation planning, and an atrial flutter planning procedure;
wherein said operator interface system comprises computer executable instructions stored in a memory for using the volume of cardiac image data and the at least one viewable image in location and navigation of an interventional tool in a 3D space of a cardiac chamber corresponding to the volume of cardiac image data;
wherein said post-processing system is adapted to display the at least one viewable image in at least one of a three-dimensional surface rendering, a three-dimensional inner surface rendering, a three-dimensional volume rendering, a three-dimensional segmented model view, MPVR, MIP, curved reformat, lumen view, and an immersible view;
wherein said post-processing system is further adapted to display a viewable image of at least one of the heart, a coronary sinus, a left ventricle, a left atrium, and a right atrium;
wherein said post-processing system is further adapted to insert at least three geometric markers for subsequent visualization, analysis and registration, each of the geometric markers corresponding with anatomical landmarks in the volume of cardiac image data, for use in the location and navigation of the interventional tool.

11. The imaging system of claim 10, wherein said post-processing system is further adapted to display a viewable image of the coronary sinus in a translucent fashion and each of the geometric markers in an opaque fashion.

12. An imaging system for use in medical intervention procedure planning, comprising:
a medical scanner system configured for generating a volume of cardiac image data;
a data acquisition system configured for acquiring the volume of cardiac image data;
an image generation system configured for generating at least one viewable image from the volume of cardiac image data;
a database configured for storing information from said data acquisition and image generation systems;
an operator interface system configured for managing at least one of said medical scanner system, said data acquisition system, said image generation system, and said database;
a post-processing system configured for analyzing the volume of cardiac image data and displaying the at least one viewable image and being responsive to said operator interface system;
wherein said operator interface system comprises computer executable instructions stored in a memory for using the volume of cardiac image data and the at least one viewable image in at least one of a bi-ventricular pacing planning, an atrial fibrillation planning, and an atrial flutter planning procedure;
wherein said operator interface system comprises computer executable instructions stored in a memory for using the volume of cardiac image data and the at least one viewable image in location and navigation of an interventional tool in a 3D space of a cardiac chamber corresponding to the volume of cardiac image data; and,
wherein the post-processing system is configured for: creating a 3D model from the volume of cardiac image data; inserting at least three geometric markers into the 3D model of the volume of cardiac image data at corresponding anatomical landmarks; and, storing in the database the 3D model of the volume of cardiac image data with the inserted at least three geometric markers and corresponding anatomical landmarks for subsequent visualization, analysis and registration, for use in the location and navigation of the interventional tool.

13. The imaging system of claim 12, wherein the operator interface system is configured to facilitate registration of the 3D model with an interventional system using the at least three geometric markers and corresponding anatomical landmarks, a centerline of a vessel used for vessel tracking, or both the at least three geometric markers and the centerline of the vessel used for vessel tracking.

* * * * *